(12) United States Patent
Nicholson et al.

(10) Patent No.: US 6,924,380 B2
(45) Date of Patent: Aug. 2, 2005

(54) CALIXARENES AND CALIXARENCE-BASED SENSORS

(75) Inventors: Graeme Peter Nicholson, Reading (GB); Mark Joseph Kan, Reading (GB); Caroline Jane Evans-Thompson, Reading (GB); Christopher William Hall, Reading (GB); Arfon Harris Jones, Reading (GB)

(73) Assignee: The Secretary of State for Defence, London (GB)

( * ) Notice: Subject to any disclaimer, the term of this patent is extended or adjusted under 35 U.S.C. 154(b) by 0 days.

(21) Appl. No.: 10/297,660

(22) PCT Filed: May 29, 2001

(86) PCT No.: PCT/GB01/02364
§ 371 (c)(1),
(2), (4) Date: Jun. 9, 2003

(87) PCT Pub. No.: WO01/96292
PCT Pub. Date: Dec. 20, 2001

(65) Prior Publication Data
US 2004/0083852 A1 May 6, 2004

(30) Foreign Application Priority Data
Jun. 10, 2000 (GB) .............................................. 0014084

(51) Int. Cl.$^7$ ........................................... C07D 323/00
(52) U.S. Cl. ...................................... 549/348; 564/162
(58) Field of Search ........................... 549/348; 564/162

(56) References Cited

U.S. PATENT DOCUMENTS 5,705,620 A    1/1998    Byrnard et al. ............. 534/829

FOREIGN PATENT DOCUMENTS

| EP | 0490631 | 6/1992 |
|---|---|---|
| WO | WO 97/17322 | 5/1997 |
| WO | WO/ 01/44175 | 6/2001 |

OTHER PUBLICATIONS

P. Cobben, et al., "Transduction of Selective Recognition of Heavy Metal Ions by Chemically Modified Field Effect Transistors (CHEMFETSs)," J. Am. Chem. Soc., vol. 114, No. 26, pp. 10573–10582 (1992).

R. Mika, et al., "Calixarene membranes on semiconductor substrates for E.I.S. chemical sensors," Electrochimica Acta, vol. 43, No. 8, pp. 841–847 (1998).

X. Yang, et al., "Polyelectrolyte and molecular host ion self–assembly to multilayer thin films: An Approach to thin film chemical sensors," Sensors and Actuators, vol. B45, pp. 87–92 (1997).

L. Chen, et al., "Calixarene–coated piezoelectric quartz crystal sensor for the detection of organic amine in liquids," Analyst, vol. 124, pp. 1787–1790 (1999).

D. Dermody, et al., "Synthesis Characterization, and Chemical Sensitivity of Self–Assembled Polydiacetylene/Calix[n] arene Bilayers," J. Am. Chem. Soc., vol. 118, No. 47, pp. 11912–11917 (1996).

H. Muller, et al., "Application of Photopolymers for the Preparation of Sodium– and Potassium Selective Matrix Membrane Electrodes," Chem. Anal., vol. 40, pp. 599–608 (1995).

*Primary Examiner*—Peter O'Sullivan
(74) *Attorney, Agent, or Firm*—Kilpatrick Stockton LLP

(57) ABSTRACT

A calixarene dimer of the general formula (I-G), comprising a first calixarene moiety I and a second calixarene moiety G, wherein: L is [—CH$_2$—] or [—O—CH$_2$—O—] and is the same or different between each aryl group; R$^5$ is H, NO$_2$, halogen, or C$_1$–C$_{10}$ aliphatic hydrocarbyl group, C$_6$–C$_{20}$ aryl group, C$_6$–C$_{20}$ hydrocarbylaryl group, any of which is optionally substituted by one or more halo or oxo groups or interrupted by one or more oxo or amide groups, and R$^5$ is the same or different on each aryl group; R$^1$ comprises a carboxy group which is or is not protonated or protected; two groups out of R$^2$, R$^3$ and R$^4$ are H; the one group out of R$^2$, R$^3$ and R$^4$ not being H comprises at least one atom of one or more of O and S, the said at least one atom being capable of causing the calixarene to be adsorbed onto the surface of the substrate; and the one group out of R$^2$, R$^3$ and R$^4$ not being H being conjugated to the second calixarene moiety G. The calixarene dimers may be incorporated into sensors. Methods of making the calixarene dimers are disclosed.

34 Claims, 10 Drawing Sheets

Fig.3.
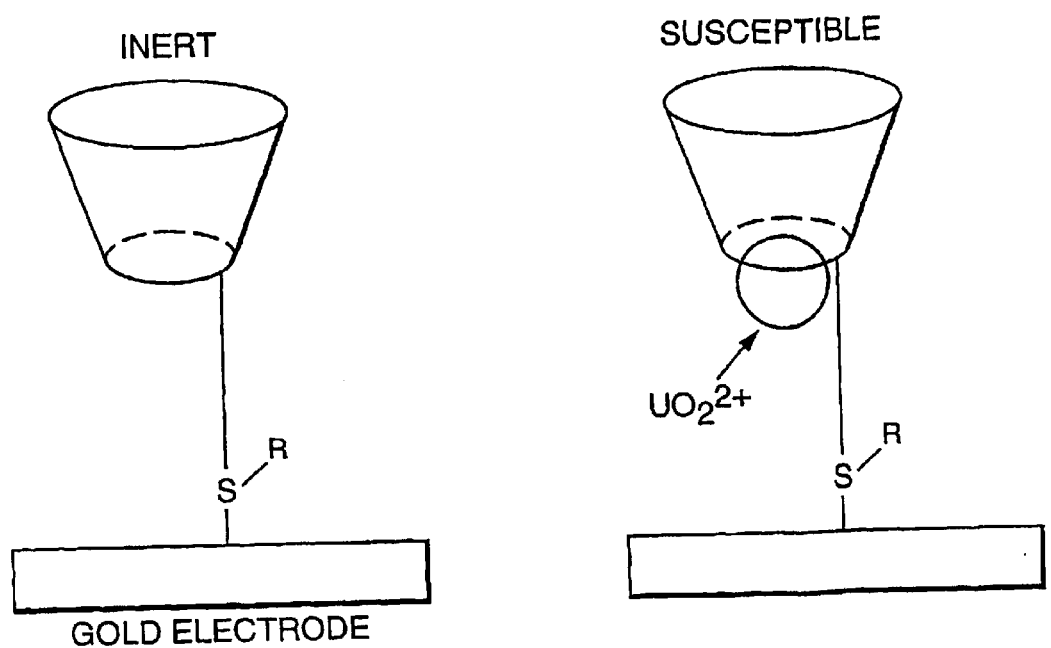
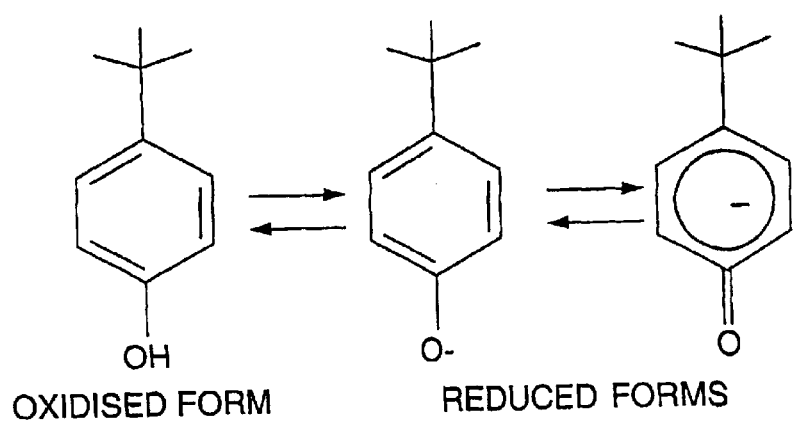

CALIXARENES AND CALIXARENCE-BASED SENSORS

This application claims priority to Great Britain Application No. 0014084.8 filed on Jun. 10, 2000 and International Application No. PCT/GB01/02364 filed on May 29, 2001 and published in English as International Publication No. WO 01/96292 A1 on Dec. 20, 2001, the entire contents of which are hereby incorporated by reference.

This invention relates to calixarene dimers and their use in the field of sensors, in particular sensors suitable for use in electrochemical analysis.

Sensors have been produced for the detection and measurement of many metal species in solution. However, there are currently no satisfactory sensors for the detection and measurement of uranium and other heavy metals in solution. Senkyr et al. (*Analytical Chem.*, Vol. 51, No. 7, p.786, 1979) utilised several acyclic ligands in polymeric membrane electrodes to produce a uranium sensor. Johnson et al (*Analyst*, Vol. 114, p.1025, 1989) used similar ligands and several cyclic ones in the development of other sensors based on polymeric membrane ion selective electrodes. While some of these sensors were found to be selective as against other ionic species, it was found that the sensors were not highly sensitive. Sensors capable of detecting the presence of Group I metals utilising calixarenes dispersed within polymeric electrodes have been reported in EP0490631. Furthermore, U.S. Pat. No. 5,705,620 discloses sensors capable of detecting calcium ions, the sensors comprising calixarene moieties immobilised in a polymeric membrane. However, none of the calixarene-based sensors were shown as being capable of detecting uranium or other heavy metals. WO97/17322 discloses that calix[4]arenes may be linked together to form a dimer species, but the properties of the dimers are not disclosed or discussed in any detail. The present invention provides novel calixarenes and sensors using calixarenes, particularly for the detection of uranium and other heavy metals in solution, those sensors giving good sensitivity.

In accordance with the present invention, a calixarene dimer of the general formula I-G comprising a first calixarene moiety of general formula I and a second calixarene moiety of formula G, formula (I-G)

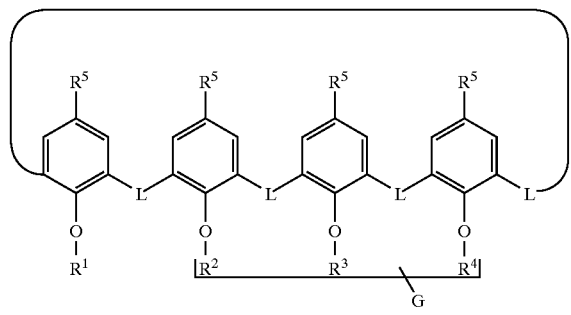

wherein:
L is [—$CH_2$—] or [—O—$CH_2$—O—] and is the same or different between each aryl group;

$R^5$ is H, $NO_2$, halogen, or $C_1$–$C_{10}$ aliphatic hydrocarbyl group, $C_6$–$C_{20}$ aryl group, $C_6$–$C_{20}$ hydrocarbylaryl group, any of which is optionally substituted by one or more halo or oxo groups or interrupted by one or more oxo or amide groups, and $R^5$ is the same or different on each aryl group;

$R^1$ comprises a carboxy group which is or is not protonated or protected;

two groups out of $R^2$, $R^3$ and $R^4$ are H;

the one group out of $R^2$, $R^3$ and $R^4$ not being H comprises at least one atom of one or both of O and S, the said at least one atom being capable of causing the calixarene to be adsorbed onto the surface of the substrate; and the one group out of $R^2$, $R^3$ and $R^4$ not being H is conjugated to the second calixarene moiety, G.

This provides an ionophore capable of chelating heavy metal ions such as uranium and cadmium. Furthermore, the molecule can be readily adsorbed onto the surface of a substrate, thus allowing sensors to be made.

The one group of $R^2$, $R^3$ and $R^4$ not being H preferably comprises any one of amide and thioamide. These groups facilitate the simple manufacture of ionophores. It is further preferred that $R^2$ and $R^4$ are H and $R^3$ comprises any one of amide and thioamide.

It is preferred that the first calixarene moiety is of a formula (II) (not shown), wherein the one group of $R^2$, $R^3$ and $R^4$ not being H conforms to the general formula (A):

[—X—Y—S—]                                      (A)

wherein X is any one of

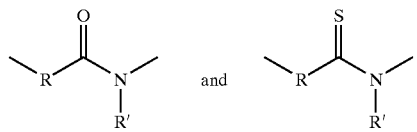

R and Y being the same or different and being $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

R' is H, $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

wherein S is conjugated to the second calixarene moiety G.

For the avoidance of confusion, it is hereby defined that S is a sulphur moiety.

This provides convenient methods of attaching sulphur-bearing moieties to the ionophore.

Alternatively, the first calixarene moiety is of formula (III) (not shown), wherein the one group of $R^2$, $R^3$ and $R^4$ not being H conforms to the general formula (E):

[—X—Y—S—]                                      (E)

wherein X is any one of

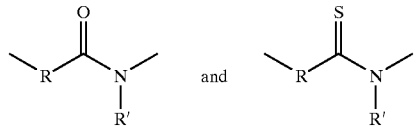

R is $(C.R^{20}.R^{21})_m$, wherein m is 0, 1, 2 or 3 and $R^{20}$ and $R^{21}$ are H, halogen or $C_1$–$C_{10}$ aliphatic hydrocarbyl group and is the same or different on each carbon.

Y is $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

R' is H, $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

wherein S is conjugated to the second calixarene moiety G.

For the avoidance of confusion, it is hereby defined that S is a sulphur moiety.

It is further preferred that the second calixarene G is also of the general formula (II) or (III).

The S group of the first calixarene may be conjugated to the S group of the second calixarene, optionally through a spacer group, the optional spacer group being $C_1$–$C_6$ aliphatic hydrocarbyl group, $C_6$–$C_{10}$ aryl group, $C_6$–$C_{16}$ hydrocarbylaryl group any of which may be optionally substituted by one of more halo or oxo groups or interrupted by one or more oxo or amide groups.

The dimers produced in this manner produce very good sensors.

It is preferred that X is ($CH_2$)CONH and Y is an aliphatic hydrocarbyl group. This choice of X gives strong chelation between the ionophore and the metal ion. Y is most preferably a methyl or an ethyl group. It is believed that a short Y (and/or short X) group improves the performance of the resulting sensor. It is preferred that the S group of the first calixarene is conjugated directly to the S group of the second calixarene, thus forming a disulphide bridging group. This gives good adhesion to a gold substrate.

In a preferred embodiment, the calixarene is of formula (V)

wherein m is 0, 1, 2 or 3 and $R^{20}$ and $R^{21}$ are H, halogen or $C_1$–$C_{10}$ aliphatic hydrocarbyl group and is the same or different on each carbon;

$R^{35}$ and $R^{36}$ are the same or different and are $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

$R^{32}$ and $R^{34}$ are the same or different and are $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

X' on each calixarene moiety are the same or different, and are O or S moieties; and $R^{37}$ is an optional spacer group, which when present is $C_1$–$C_6$ aliphatic hydrocarbyl group, $C_6$–$C_{10}$ aryl group or $C_6$–$C_{16}$ hydrocarbylaryl group any of which maybe optionally substituted by one of more halo or oxo groups or interrupted by one or more oxo or amide groups.

It is preferred that $R^{31}$ and $R^{33}$ are mutually the same. It is also preferred that $R^{32}$ and $R^{34}$ are mutually the same. It is further preferred that $R^{35}$ and $R^{36}$ are mutually the same. It is preferred that one or both of $R^{31}$ and $R^{33}$ are conjugated to $R^3$ of their respective calixarene moieties. It is preferred that $R^{31}$, $R^{33}$, $R^{32}$ and Re are relatively short. If any of $R^{31}$, $R^{32}$, $R^{33}$ and $R^{34}$ are $C_1$–$C_{10}$ aliphatic hydrocarbyl groups, then it is preferred that these groups are $C_1$–$C_5$ aliphatic formula (V)

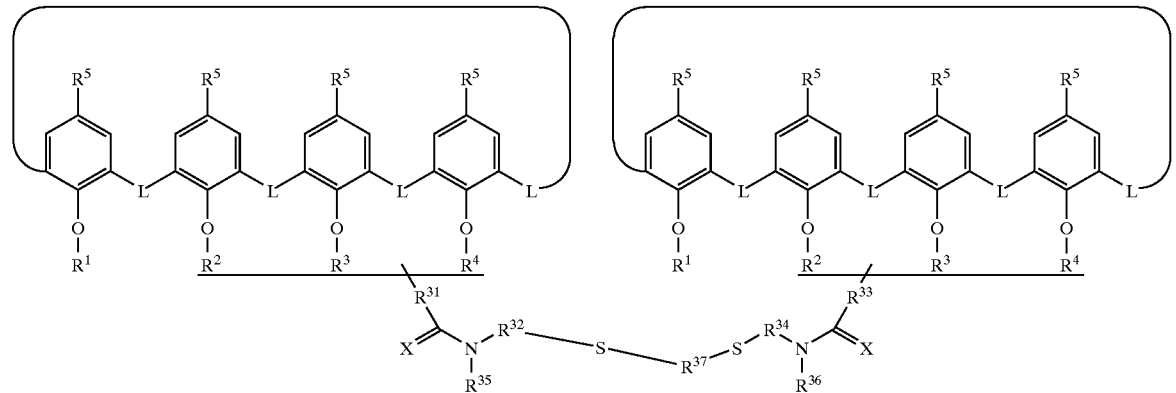

wherein

L is [—$CH_2$—] or [—O—$CH_2$—O—] and is the same or different between each aryl group;

$R^5$ is H, $NO_2$, halogen, or $C_1$–$C_{10}$ aliphatic hydrocarbyl group, $C_6$–$C_{20}$ aryl group, $C_6$–$C_{20}$ hydrocarbylaryl group, any of which is optionally substituted by one or more halo or oxo groups or interrupted by one or more oxo or amide groups, and $R^5$ is the same or different on each aryl group;

$R^1$ is the same or different on each calixarene moiety comprises a carboxy group which is or is not protonated or protected;

two groups out of $R^2$, $R^3$ and $R^4$ on each calixarene moiety are H;

the one group out of $R^2$, $R^3$ and $R^4$ not being H on each calixarene moiety is the respective one of $R^{31}$ and $R^{33}$;

$R^{31}$ and $R^{33}$ are the same or different and are $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups; or $(C.R^{20}.R^{21})_m$, hydrocarbyl groups, most preferred that these groups are $C_1$–$C_3$ aliphatic hydrocarbyl groups.

It is preferred that L is [—$CH_2$—] between each of the aryl groups and that $R^5$ is a tertiary butyl group. It is most preferred that $R^5$ is an electron-withdrawing group, such as $NO_2$.

The carboxy group $R^1$ may conform to the general formula (B):

[—Z—COOR¹⁰]     (B)

wherein Z is a $C_1$, a $C_2$ or a $C_3$ carbon chain which is a part of an aliphatic hydrocarbyl group, aryl group or hydrocarbylaryl group, any of which is optionally substituted by one or more halo, oxo or nitro groups; and $R^{10}$ is H or a protecting group being a salt or an ester group. It is preferred that $R^{10}$ is H and the aliphatic hydrocarbyl group, aryl group or hydrocarbylaryl group of formula (B) are substituted by one or more groups which cause a reduction in the pKa of the carboxylic acid group with respect to an unsubstituted molecule, This increases the ability of the ionophore to complex with heavy metals.

Alternatively, $R^1$ is of the general formula (C):

$$[-(C.R^6.R^7)_n-COOR^{10}] \quad (C)$$

wherein n is 1, 2 or 3 and $R^6$ and $R^7$ are H or halogen and is the same or different on each carbon; and $R^{10}$ is H or a protecting group being a salt or an ester group.

In a further alternative embodiment, $R^1$ is of the general formula (D):

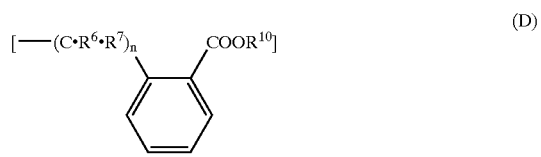

wherein n is 0 or 1 and $R^6$ and $R^7$ are H or halogen and is the same or different on each carbon and wherein the phenyl ring of the bernzoic acid group is optionally substituted by one or more halo, oxo or nitro groups; and $R^{10}$ is H or a protecting group being a salt or an ester group. It is preferred that $R^{10}$ is H and the phenyl ring of the benzoic acid of formula (D) is substituted by one or more groups which cause a reduction in the pKa of the carboxy group with respect to an unsubstituted molecule.

When $R^1$ is of the formula (C) or (D), then it is preferred that n is 1 and $R^6$ and $R^7$ are both H. This gives an acid group with a strong affinity for heavy metal ions, the chelating oxygen atom being in a good position for chelation due to n being 1.

As a further alternative, some or all of phenyl groups of the calixarene ring are further peripherally substituted.

In accordance with a second aspect of the present invention a sensor comprises a calixarene dimer in accordance with the present invention. It is preferred that the sensor further comprises a substrate wherein the calixarene is adsorbed onto the surface of the substrate. This provides a sensor sensitive to low levels of heavy metals, wherein there is direct molecular contact between the electrode and the active ionophore.

The substrate may comprise one or more metals, preferably gold. This provides an inexpensive and effective sensor. Gold allows good adsorption of ionophores onto the surface of the electrode.

In accordance with a third aspect of this invention, a method for sequestering metals comprises contacting the metals with a calixarene dimer in accordance with the present invention. This provides a good way of removing even low levels of metals from solution. The method is preferably carried out at a pH of between about 2 and about 11. The pH is preferably buffered.

In a most preferred embodiment of this aspect of the invention, the method comprises:

(i) dissolving the calixarene in an hydrophobic organic solvent;

(ii) mixing the organic solvent with an aqueous phase containing metal ions;

(iii) agitating the organic solvent and aqueous phase together; and (iv) recovering the metal from the organic phase.

This allows the extraction of low levels of heavy metal from aqueous solution. The metal is preferably selected from any one of U, Cd, Sr, Ca, a Lanthanide and Lu.

In accordance with a fourth aspect of the present invention, a process for preparing a calixarene dimer comprising the use of cystariline dihydrochloride to conjugate two calixarene moieties.

The invention will now be described by way of example only with reference to the following figures, of which:

FIG. 3 is a schematic representation of the mechanism by which it is expected that calixarenes deployed in sensors according to the present invention undergo reduction and oxidation;

REACTION SCHEME 1

Figure 1:
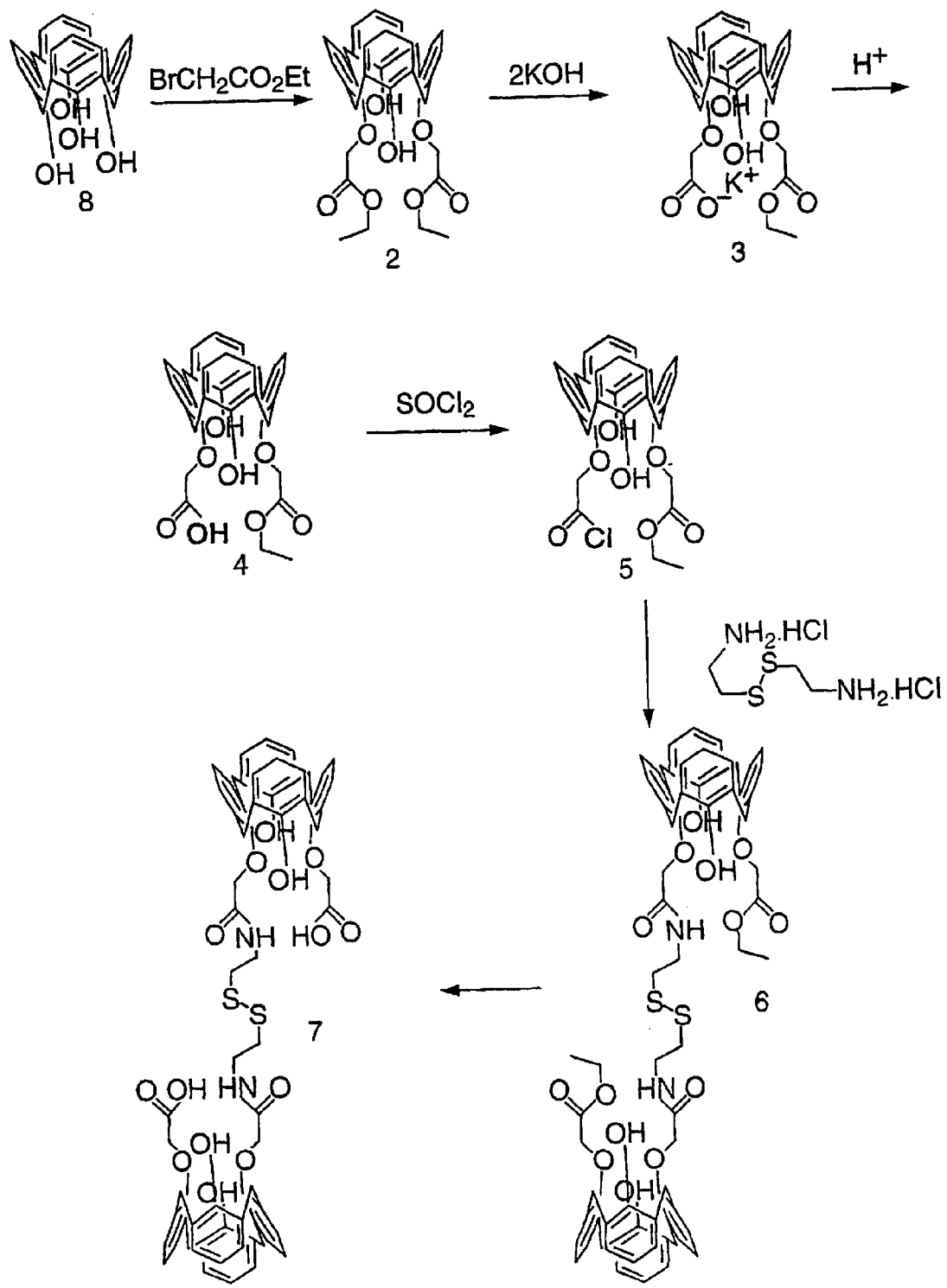
FIG. 1 is a reaction scheme for the production of calixarene dimers in accordance with the present invention.

Dimers 6 and 7 in accordance with the present invention are synthesised in accordance with the reaction scheme shown in FIG. 1.

Calix[4]arene 8 was prepared by standard procedures via the debutylation of tertiary butyl calix[4]arene with aluminium chloride (Arduini and Casnati, Macrocyle Synthesis, Ed. David Parker, 1995, Oxford).

Synthesis of 2

A mixture of calix[4]arene 8 (1.0 g, 2.35 mmol), potassium carbonate (0.71 g, 5.17 mmol), acetone (50 cm$^3$) and bromoethylacetate (0.57 cm$^3$, 5.17 mmol) was stirred at room temperature, under nitrogen, for 6 days. The mixture was then evaporated to dryness, then slurried with ethyl acetate and hexane, filtered and the filtrate evaporated to dryness. This filtrate was then slurried with DCM and filtered and the filtrate evaporated to dryness, then recrystailised from ethyl acetate and chloroform giving 2 (0.33 g), m.p., 183° C. The structure of 2 was verified by NMR and mass spectroscopy.

Synthesis of 3

A mixture of 2 (3.93 g, 6.6 mmol), ethanol (240 cm$^3$) and potassium hydroxide (28.6 cm$^3$ of a 0.46 M solution in ethanol, 13.2 mmol) was stirred at reflux for 2.5 h. The mixture was then evaporated to dryness and dried in a vacuum oven at 100° C. for 2 h, giving a solid.

Preparation of 4

DCM (100 cm$^3$) and dilute hydrochloric acid (50 cm$^3$) were added to 3 obtained above, and the mixture shaken.

The mixture was allowed to settle and the DCM layer separated and evaporated to dryness. Next, acetic acid and ethanol were added to the aqueous layer and mixture filtered and the solids combined with the DCM soluble solids (3.66 g). The solid was then purified on silica, eluting with DCM, hexane and acetic acid (2:2:1), giving 4 (0.80 g), m.p., 244° C. The structure of 4 was verified by NMR and mass spectroscopy.

Synthesis of 5

A mixture of 4 (0.50 g, 0.88 mmol), DCM (10 cm$^3$) and thionyl chloride (1.0 cm$^3$) was stirred under nitrogen, under reflux for 3 h. An IR spectrum of the mixture confirmed that 4 had been converted to the acid chloride ester, 5, $\upsilon_{max}$ 1809 (COCl), 1752 (CO$_2$Et). Next, DCM and thionyl chloride were removed by distillation under reduced pressure, giving crude 5, which was used without further purification.

Synthesis of 6

The acid chloride 5 (0.50 g, 0.88 mmol) was dissolved in DCM (10 cm$^3$) and added to cystamine hydrochloride (0.10 g, 0.44 mmol) and triethylamine (0.5 cm$^3$), under nitrogen, with siring. After a few minutes, the mixture rapidly darkened. The reaction was monitored by the disappearance of the acid chloride peak and after 3 days, the mixture was evaporated to dryness. This solid was then slurried with hot ethylacetate and filtered, giving a solid, assumed to be unreacted cystamine hydrochloride and triethylamine hydrochloride (0.34 g). The filtrate was evaporated to dryness (0.43 g), then column chromatography on silica, eluting DCM and hexane gave unreacted 4 (0.30 g) and 6 (0.02 g, 2%). The structure of 6 was verified by NMR, IR and mass spectroscopy.

Synthesis of 7

Reaction of the acid chloride 6 with ethanolic potassium hydroxide did not yield the expected acid product 7. However, those skilled in the art will recognise that other agents, such as Ba(OH)$_2$ are available to perform this reaction.

REACTION SCHEME 2

Figure 2:
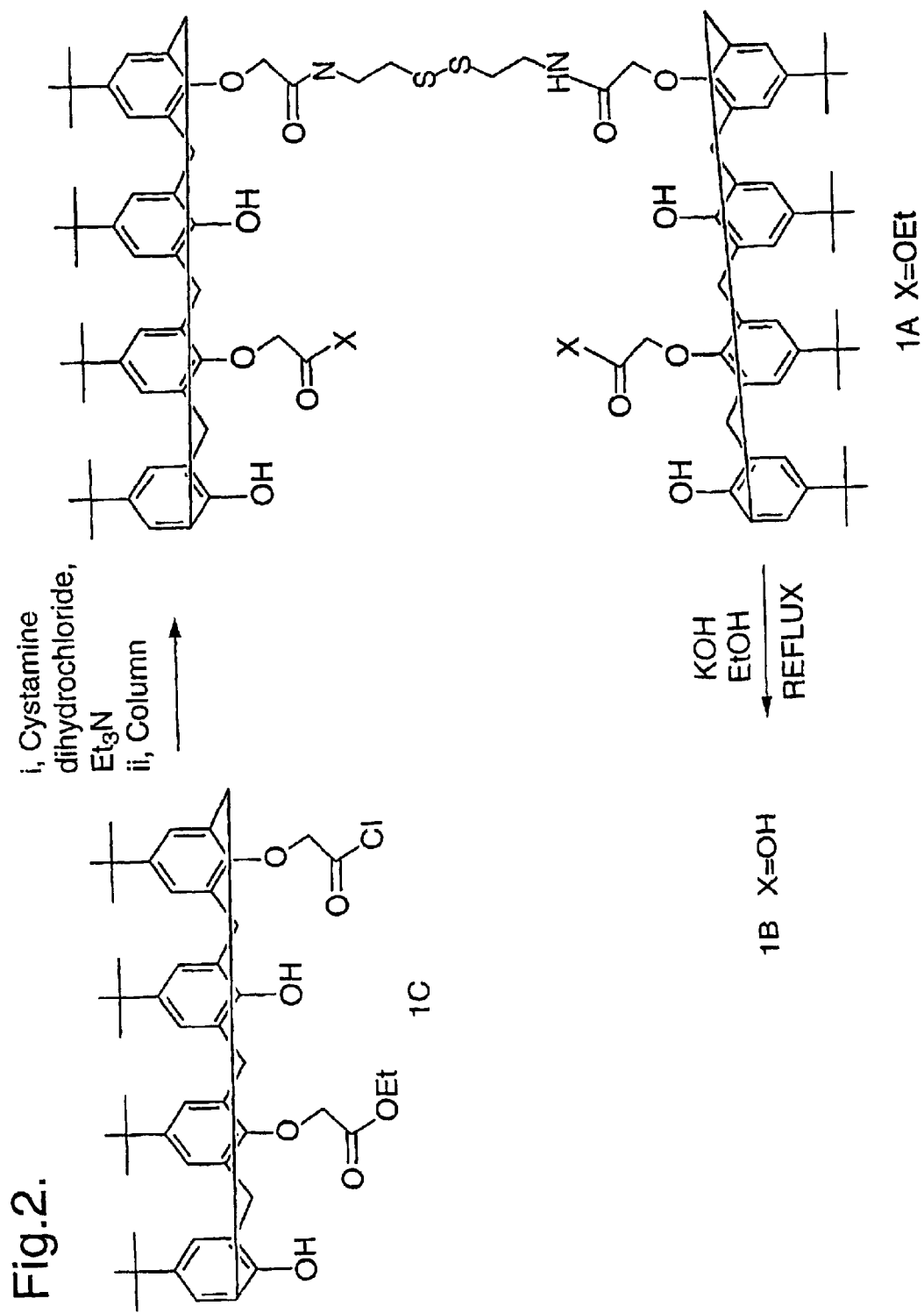
FIG. 2 is a reaction scheme for the production of more calixarene dimers in accordance with the present invention.

Dimers 1A and 1B in accordance with the present invention are synthesised in accordance with the reaction scheme shown in FIG. 2.

Synthesis of 1A

The acid chloride 1C (analogous to 5 above) maybe produced using the general methodology described above for the manufacture of 5, but using tertiary butyl calix[4]arene as a starting material, instead of calix[4]arene. The acid chloride 1C (0.5 g, 0.63 mmol) was added to a mixture of triethylamine (0.3 cm$^3$), cystamine dihydrochloride (0.071 g, 0.31 mmol) and dichloromethane (20 cm$^3$) with stirring, under nitrogen at room temperature. The mixture was then stirred at room temperature for 18 hours. Water (20 cm$^3$) and dilute hydrochloric acid (20 cm$^3$) were added and the mixture extracted into dichloromethane. The dichloromethane was then evaporated to give a solid (0.75 g). Column chromatography on silica, eluting cyclohexane-:ethylacetate (3:2) gave ionophore 1A (0.11 g). The structure was confirmed by infra-red (IR) and nuclear magnetic resonance (NMR) spectroscopy. Note that the synthesis of the acid chloride IC is disclosed in WO97/17322.

Synthesis of 1B

A mixture of 1A (0.14 g, 0.08 mmol), ethanol (20 cm$^3$) and ethanolic potassium hydroxide solution (0.50 cm$^3$ of 0.43M solution) was refluxed for 2 days. The mixture was cooled and acidified with dilute hydrochloric acid. The resulting solid was filtered from the suspension and dried (0.025 g). The solid was recrystallised from a mixture of dichloromethane and methanol, giving partially purified 1B. The structure of 1B was confirmed by IR and NMR spectroscopy. Small amounts of impurities were found in the partially purified 1B.

Despite this patent application disclosing the synthesis of only a limited number of calixarenes in accordance with the present invention, those skilled in the art will realise that the claimed molecules can be readily synthesised using the teaching of this document in combination with that of WO97/17322. WO97/17322, inter alia, teaches how to modify the periphery of the calixarene moiety.

It is anticipated that the thioamide analogues of 1A and 6 can be synthesised by refluxing 1A and 6 respectively with Lawesson's reagent. Furthermore, it is anticipated that one can readily synthesise dimers where calixarene moieties I and G are not the same. The moieties I and G would each contain reactive acid chloride groups. I and G would then be reacted with a trialkylamine and cystamine dihydrochloride to form dimers, as outlined in the synthesis of 1A and 6 above. Three dimer structures would be formed, and these could be separated if desired.

These ionophores can be readily used in sensors as is now discussed.

A sensor in accordance with the present invention comprises a calixarene in accordance with the present invention. It is preferred that the calixarene is adsorbed onto the surface of an electrode. The term 'adsorbed' is intended to include chemically adsorbed and physically adsorbed. There are several ways of depositing the calixarene onto the surface of the electrode, such as spin coating, Langmuir Blodgett deposition and plasma coating. However, the easiest manner of making such a sensor is to immerse the electrode into a solution of the calixarene. This causes a nominal monolayer of the calixarene to form on the surface of the electrode. The resulting electrode is often referred to as a chemically modified electrode. The calixarene is adsorbed onto the surface of the electrode but it is unclear as to whether the layer formed is a true monolayer.

The sensor can then be characterised by cyclic voltammetry (CV), a technique well-known to those skilled in the art. A description of this technique can be found in "Instrumental methods in electrochemistry" by Greef, Peat, Peter, Pletcher and Robinson, published by Ellis Horwood.

The sensor is immersed in a suitable ionic solution and CV used to probe the interaction between the sensor and ions. Two peaks will typically be observed in the CV cycle. One of these represents oxidation of a component of the sensor and the other represents the corresponding reduction reaction. The nature, and quantity, of the ion adsorbed by the ionophore may effect the redox characteristic of the said component. For example, the chelation of different ions has been found to alter the spacing between the two peaks, and increasing concentrations of ions have been found to increase the height of the peaks. Hence, such sensors in accordance with the present invention have been found to provide excellent performance.

Examples of the manufacture and characterisation of sensors in accordance with the present invention are now described.

EXAMPLE 1

Figure 4:
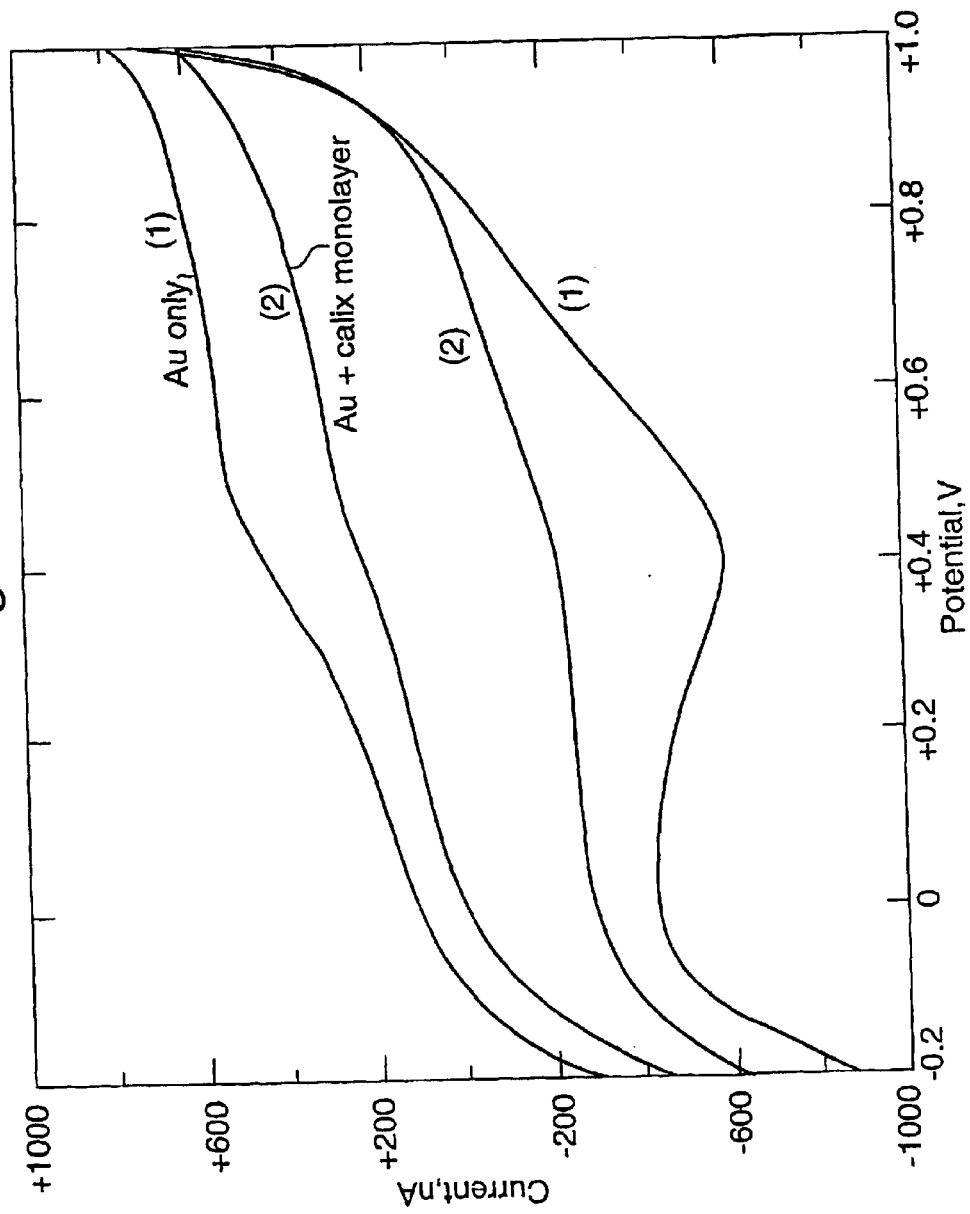
FIG. 4 is a voltamogram obtained from a sensor in accordance with the present invention, the sensor not being in contact with a test solution.

A gold electrode with an exposed surface area of 1–2 mm$^2$ was immersed for 15 minutes in a 0.2 mM solution of the calixarene 1B (FIG. 2) in dichloromethane. It is anticipated that the interaction between the sulphur atoms of the thiol group and the gold atoms of the electrode cause the ionophore to be adsorbed onto the electrode surface as is illustrated schematically in FIG. 3. The interaction between the sulphur and gold atoms is strong, yet the exact nature of the interaction is unknown This sensor was characterised using CV. An estimate of 30% monolayer coverage was determined by measuring the reduction in area of the CV curve for the electrode bearing the monolayer film compared to the electrode bearing no film (FIG. 4).

EXAMPLE 2

Figure 5:
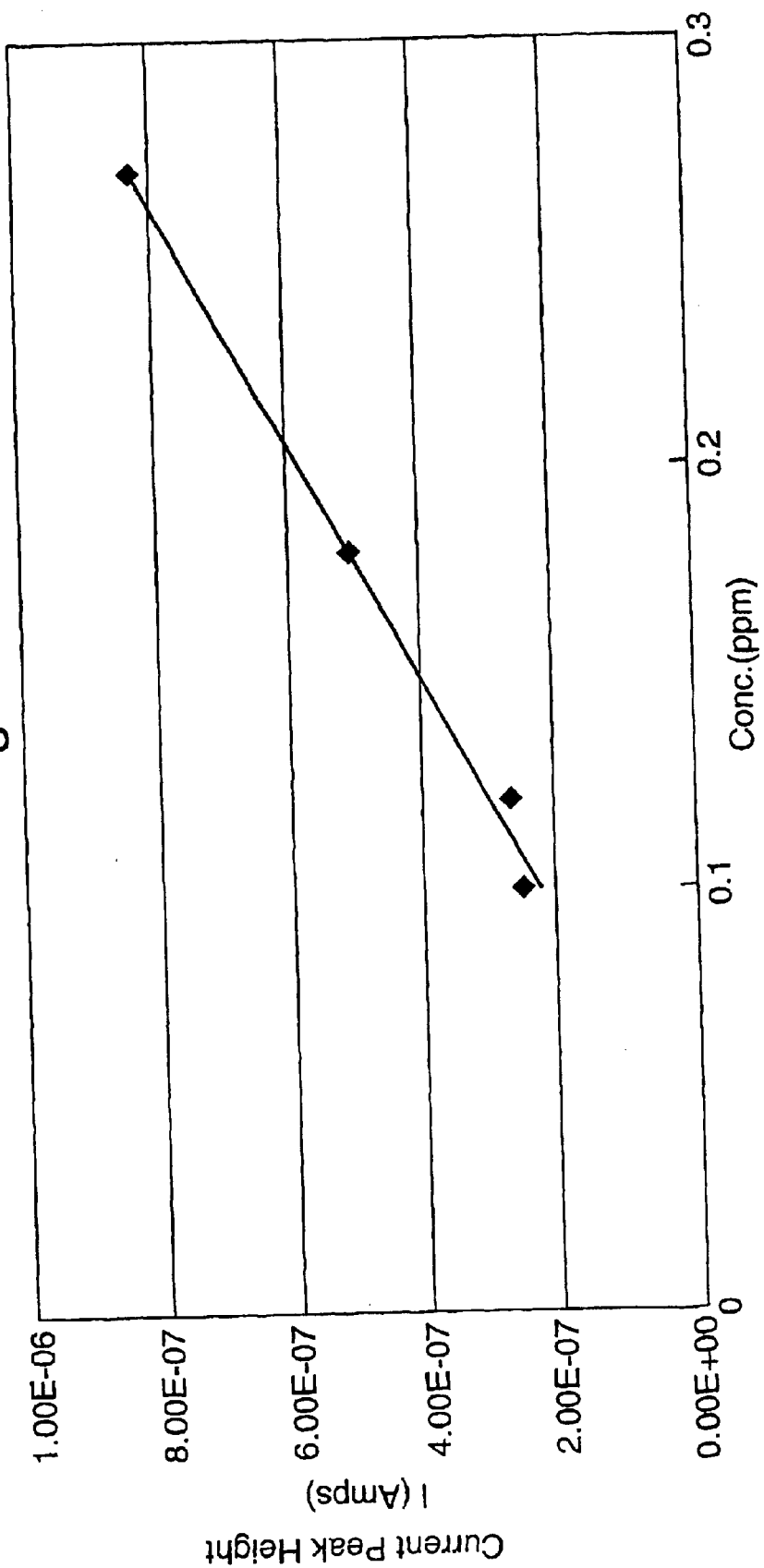
FIG. 5 is a graph showing the current peak height in a voltamogram as a function of the concentration of uranium ions as measured by a sensor in accordance with the present invention.

A sensor as produced using the methodology of example 1 was characterised by measuring the CV characteristics of the sensor as a function of uranium ion concentration at pH=2 and with a constant potential sweep rate of 100 mV/s. The sensor was immersed in the test solution for 15 minutes prior to taking a reading. The data indicate a linear increase in the current peak height with increase in ion concentration over the range 100–300 ppb (FIG. 5). However, it is unclear whether the relationship between peak height and ion concentration is linear below 100 ppb. These data illustrate that a sensitive sensor can be easily achieved using the present invention.

EXAMPLE 3

Figure 6:
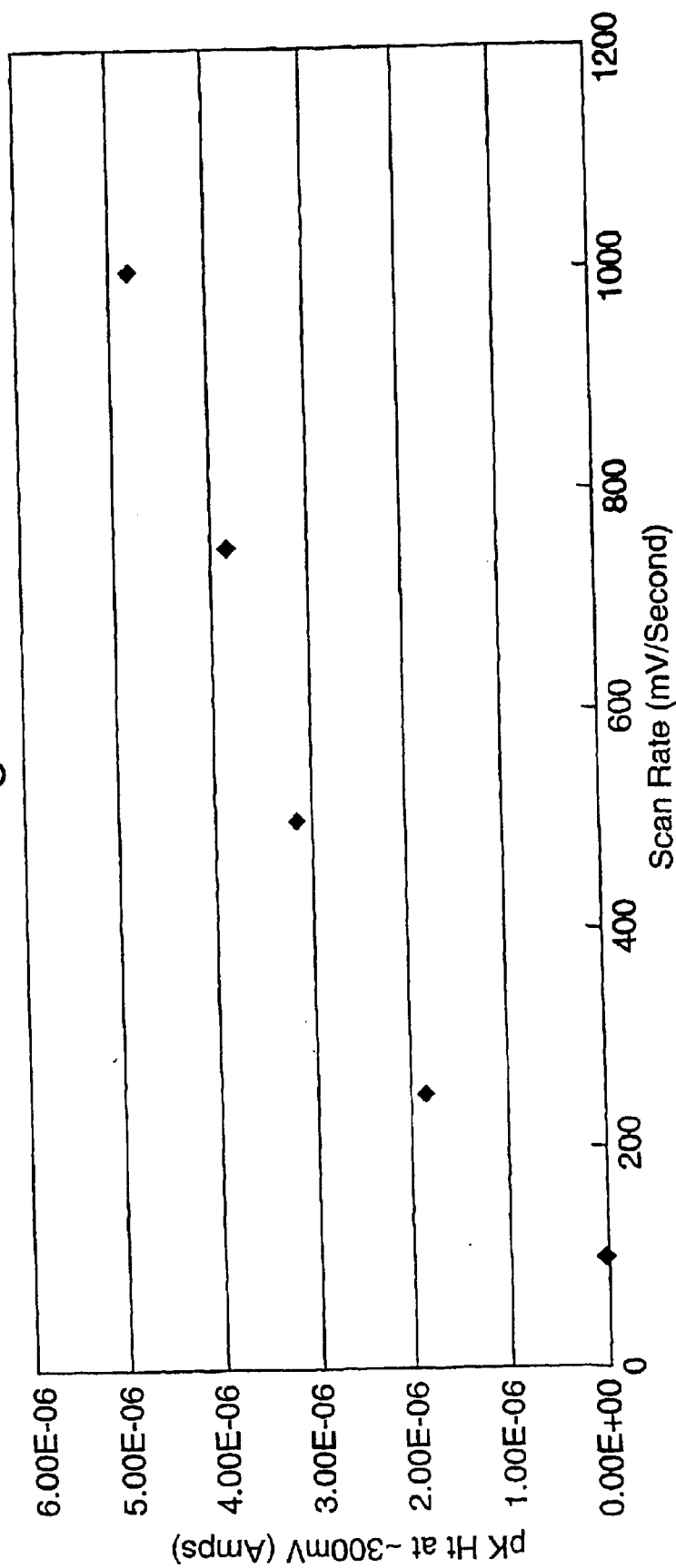
FIG. 6 is a graph showing the current peak height in a voltamogram as a function of the scan rate as measured by a sensor in accordance with the present invention.

Another sensor produced using the methodology of example 1 was characterised using cyclic voltammetry. The height of the oxidation and reduction peaks are also dependent on the potential sweep rate, with an increase in sweep rate giving a sub-linear increase in peak height (FIG. 6). It is believed that an increased scan rate gives a taller peak due to an experimental artefact of there being fewer data points accumulated as the scan rate increases.

EXAMPLE 4

Figure 7:
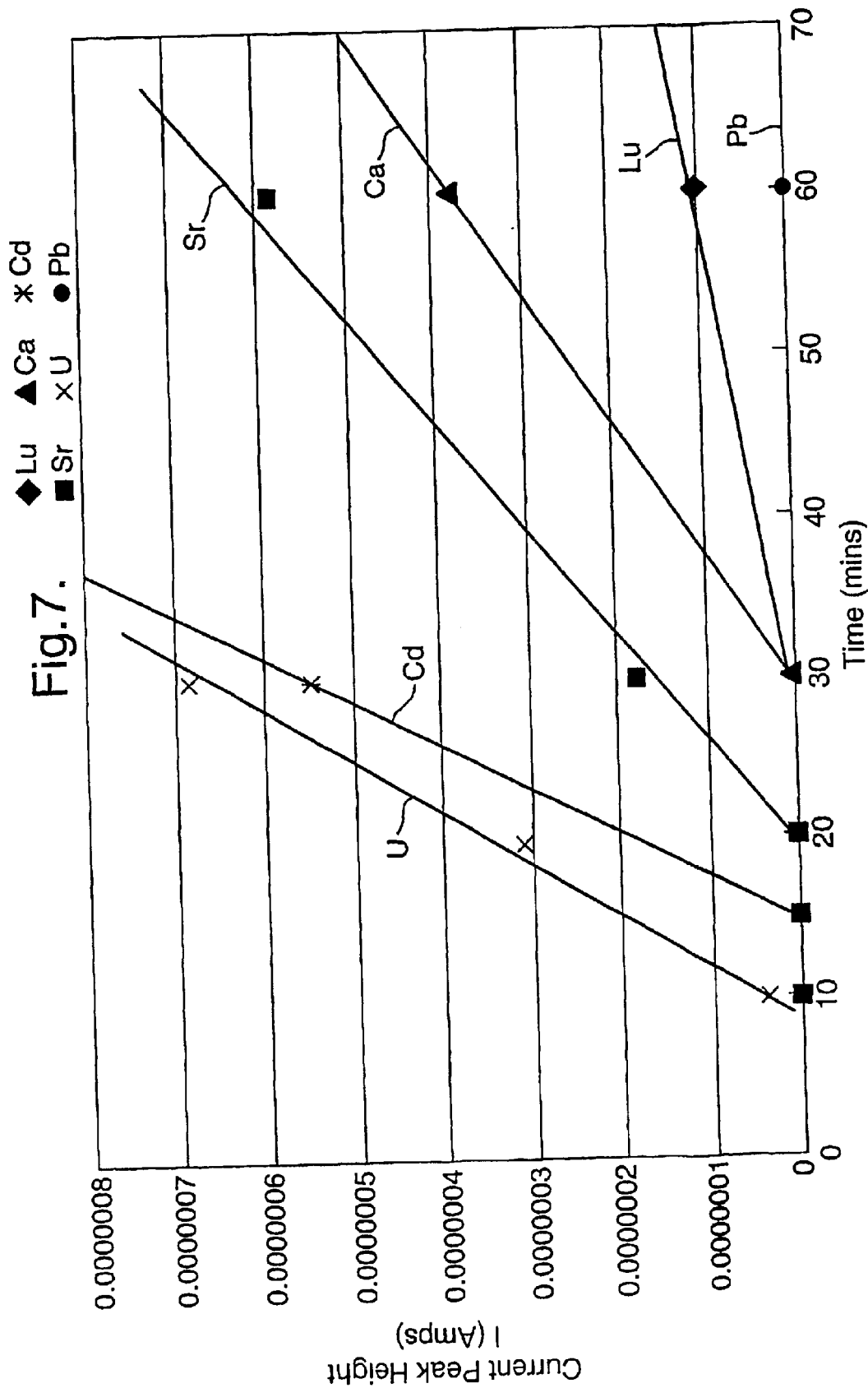
FIG. 7 is a graph showing the current peak height in a voltamogram as measured by a sensor in accordance with the present invention as a function of extraction time for a variety of metal ions.

The responses (current peak height) of sensors produced in accordance with the methodology of example 1 were monitored as a function of the time and as a function of cation Each sensor was immersed in a solution of one of various cations (U, Pb, Cd, Sr, Ca, Lu, pH=2, 500 ppb solutions) and the CV response was measured, giving the results shown in FIG. 7. This indicates that in each case there is a period for which no response is measured by the sensor i.e. no oxidation or reduction peaks were observed in the CV curves. This period was shortest for U but was still reasonably long at approximately 9 minutes. U, Sr, Cd, Lu and Ca generated a response in the sensor, but Pb did not. This illustrates that the sensor is somewhat selective, with a greater affinity for U, Cd and Sr. Furthermore, for each cation there is a linear response in current peak height with increasing extraction time. It was also noted that the difference in voltage between the oxidation and reduction peaks was a function of the ion chelated to the calixarene molecule as shown below in Table 1.

TABLE 1

Positions of the oxidation and reduction peaks for several types of metal ion

| Analyte | Position of oxidation peak (mV) | Position of reduction peak (mV) | Difference between peak positions (mV) |
|---|---|---|---|
| U | 304 | 86 | 218 |
| Cd | 289 | 98 | 191 |
| Ce | 287 | 80 | 207 |
| Lu | 312 | 91 | 221 |
| Sr | 323 | 24 | 299 |
| Ca | 295 | 112 | 183 |

Hence, the difference in voltage between the two peaks may be used to identify the ion detected by the sensor. However, the results from an analysis of a mixture of U, Cd and Ce ions gave results that were inconsistent with those shown in Table 1.

EXAMPLE 5

Figure 8:
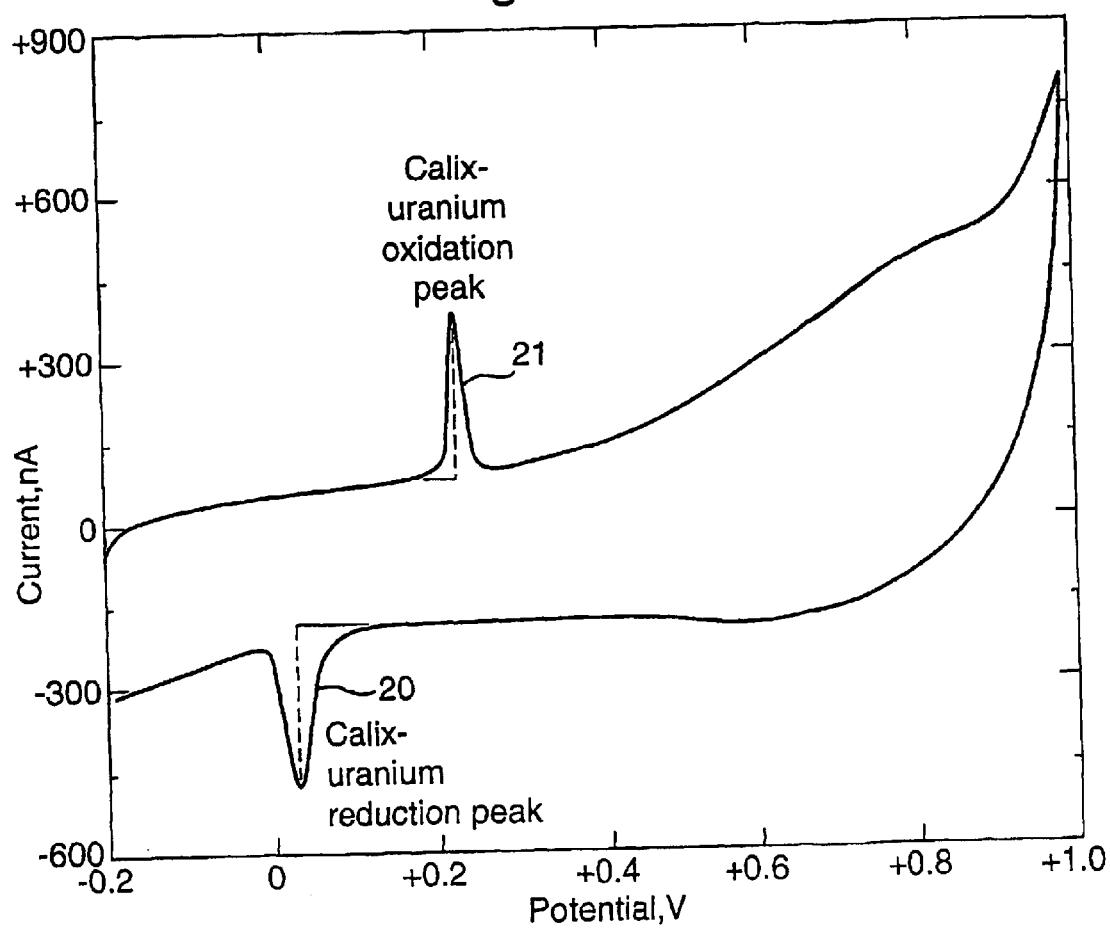
FIG. 8 is a cyclic voltamogram generated using a sensor in accordance with the present invention.
Figure 9:
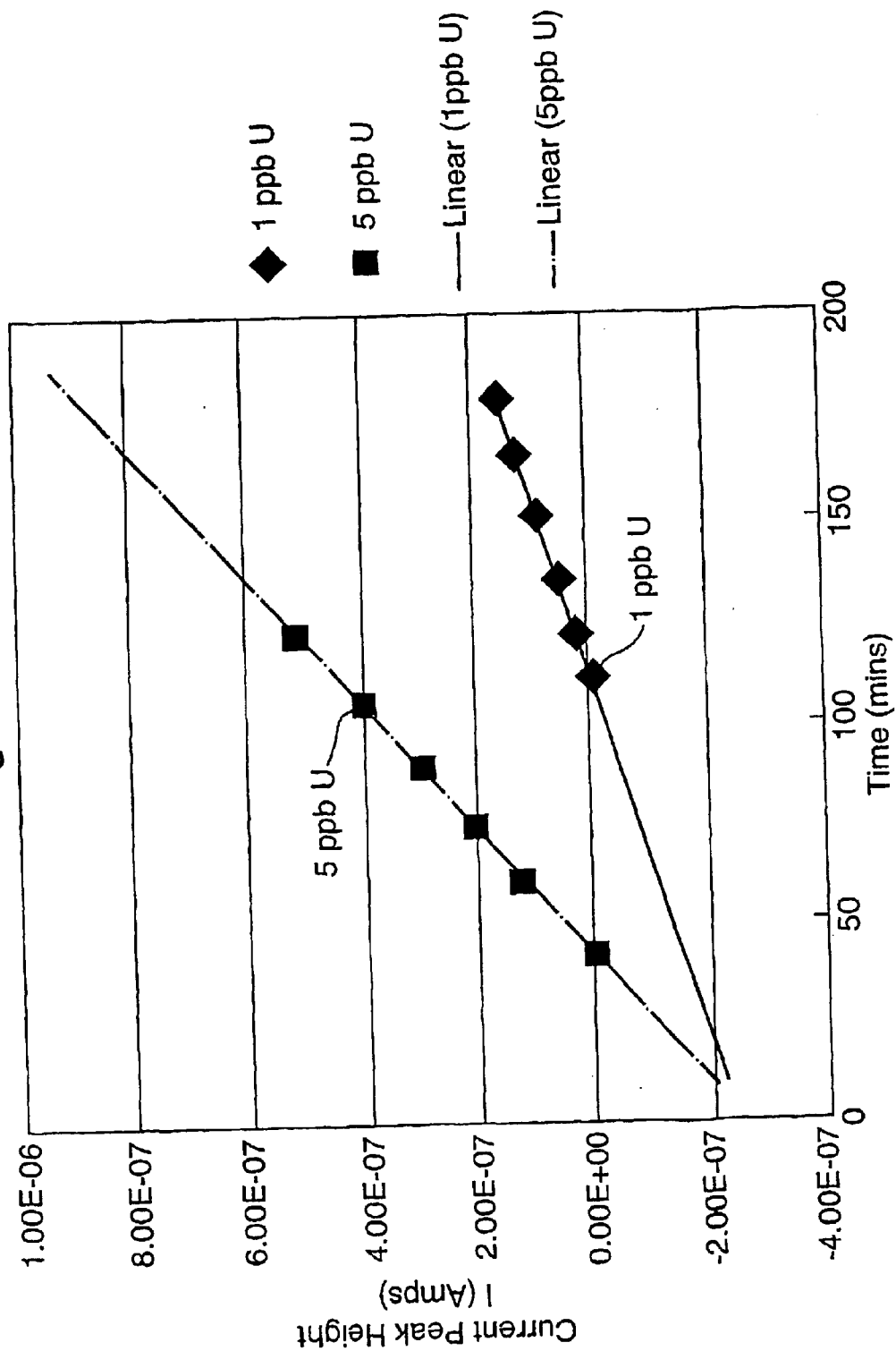
FIG. 9 is a graphical representation of the current peak height from a sensor in accordance with the present invention as a function of time and uranium ion concentration.

A layer of compound 1B, a calixarene dimer bridged with a disulphide group, was deposited onto a gold substrate using the methodology of example 1. The sensor was tested in accordance with the general methodology of examples 1 and 2. FIG. 8 shows a cyclic voltamogram generated using this sensor immersed in an aqueous uranium ion solution. The two peaks, 20, 21 indicate reduction and oxidation processes respectively. FIG. 9 shows the current peak height from the sensor as a function of time and the concentration of uranium. This demonstrates that the sensor can detect ultra-low levels of uranium, down to 1 ppb, given sufficient time for the electrode to react This also confirms that the current peak height varies linearly with the time for which the sensor is exposed to the solution, there being an initial time period in which the sensor does not respond. The speed of the response of the detector (i.e. the rate of change in the current peak height for a given change in time) increases as the concentration of the solution increases, although it appears that the relationship between speed of response and concentration is sub-linear.

Figure 10:
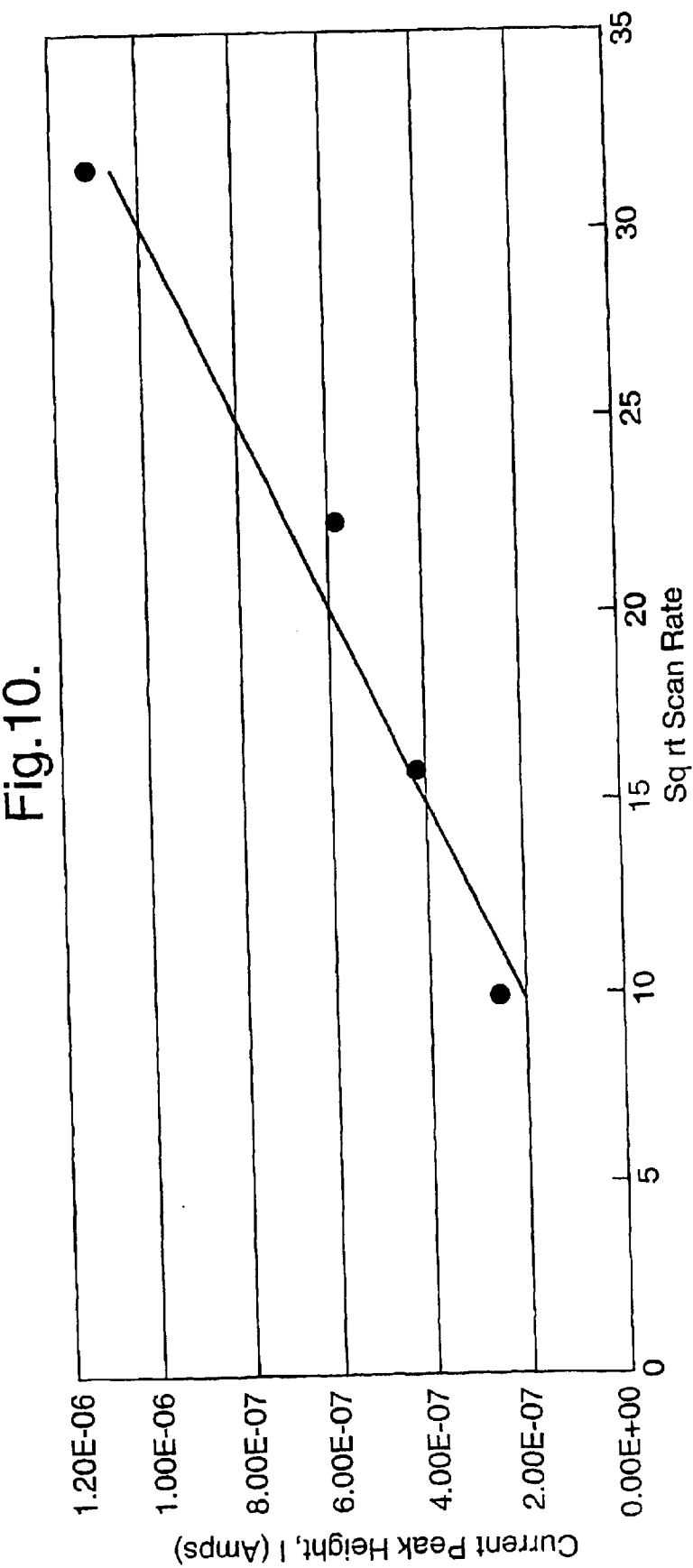
FIG. 10 is a graphical representation of the current peak height from a sensor in accordance with the present invention as a function of the square root of the scan rate.

The current peak height was measured as a function of the potential scan rate as shown in FIG. 10. Note that the current peak height increases as the scan rate increases in a sub-linear manner. This is thought to be an artefact of the experimental set-up and is consistent with the results of example 3.

It is not known whether the calixarene dimer 1B remains intact when deposited onto the surface of the electrode. It is quite possible that the disulphide bridge breaks, giving 2 monosulphide or thiol monomers.

The excellent performance of the calixarene-based sensors is surprising: it has been shown by Beer (*Inorganic Chemistry*, 1997, 36, 5880) that chemical oxidation of p-tert-butylcalix[4]arene bis esters and amides gives p-tert-butylcalix[4]diquinones, and these calix[4]diquinones have been shown to display anodic shifts in their reduction potentials in the presence of group 1 or 2 metal, ammonium and alkylammonium complexes. However, electrochemical oxidation of p-tert-butylcalix[4]arenes in the presence or absence of metal cations has not been observed or considered in the literature (for example, see chapter 7 in "Calixarenes Revisited" by C. David Gutsche or "Calixarenes in Action" by Luigi Mandolini and Rocco Ungaro and references therein).

It was thought that one had to incorporate additional moieties into the system, those moieties readily undergoing redox reactions and being placed in electrostatic proximity to the ionophore (Paul D. Beer, J. Chem Soc., Dalton Trans., 1999, 1897). In such a system, the complexation of a metal ion (uranium, for instance) into the calixarene molecule would alter the redox characteristics of the nearby added moiety and hence the system would act as a sensor.

The reasons for the unexpected excellent performance of the sensors in accordance with the present invention are unclear but may be related to the relatively high density of calixarene ions on the surface of the detector and the relatively short distance between the calixarene group and the substrate. As mentioned above, it was previously thought that the calixarene moiety was inert to redox reactions, even when it incorporated metal ions. However, it has been demonstrated that a component of the sensors in accordance with the present invention is involved in a redox reaction. It is herein tentatively proposed that the redox activity of the sensors can be explained by the schematic representation of FIG. 3. The proximity of both the uranyl ion and the group undergoing redox reactions to the electrode surface probably contribute to the superior performance of the sensors in accordance with the present invention.

Notwithstanding the correctness of the above interpretation of the mechanism of the redox reaction, it has been shown that sensors comprising calixarenes adsorbed onto the surface of an electrode are readily achievable.

It is clear from the present patent application that the calixarene dimers in accordance with the present invention are capable of extracting certain metal ions from solution. It is therefore to be expected that these dimers can be readily used in the extraction methods found in WO97/17322.

What is claimed is:

1. A calixarene dimer of the general formula I-G comprising a first calixarene moiety of general formula I and a second calixarene moiety G, formula (I-G)

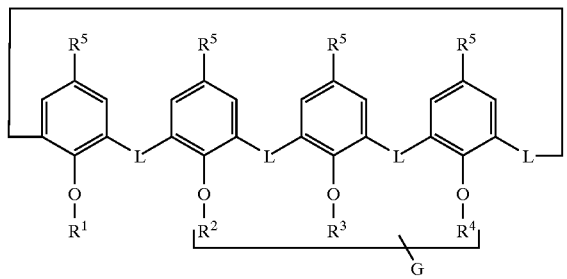

wherein:
L is [—$CH_2$—] or [—O—$CH_2$—O—] and is the same or different between each aryl group;
$R^5$ is H, $NO_2$, halogen, or $C_1$–$C_{10}$ aliphatic hydrocarbyl group, $C_6$–$C_{20}$ aryl group, $C_6$–$C_{20}$ aryl group, $C_6$–$C_{20}$ hydrocarbylaryl group, any of which is optionally substituted by one or more halo or oxo groups or interrupted by one or more oxo or amide groups, and $R_5$ is the same or different on each aryl group;
$R^1$ comprises a carboxy group which is not protonated or protected;
two groups out of $R^2$, $R^3$ and $R^4$ are H; the one group out of $R^2$, $R^3$ and $R^4$ not being H comprises at least one atom of one or both of O and S, the said at least one atom being capable of causing the calixarene to be adsorbed onto the surface of the substrate; and
the one group out of $R^2$, $R^3$ and $R^4$ not being H is conjugated to the second calixarene moiety, G, wherein, the one group of $R^2$, $R^3$ and $R^4$ not being H conforming to the general formula (A):

[—X—Y—S—]     (A)

wherein X is any one of

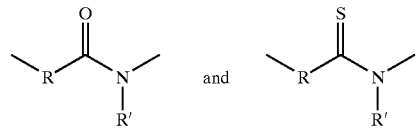

R and Y being the same or different and being $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;
R' is H, $C_1$–$C_{10}$ aliphatic hydrocarbyl group, $C_6$–$C_{10}$ aryl group or $C_6$–$C^{20}$ hydrocarbylaryl group, any of which may be optionally substituted by one or more halo or oxo groups or interrupted by one or more oxo or amide groups;
wherein S is conjugated to the second calixarene moiety G.

2. The dimer of claim 1 wherein the one group of $R^2$, $R^3$ and $R^4$ not being H comprises thioamide or amide.

3. The dimer of claim 2 wherein $R^2$ and $R^4$ are H and $R^3$ comprises thiomide or amide.

4. The dimer of claim 1 wherein the structure of the first calixarene moiety is known as formula (III), the one group of $R^2$, $R^3$ and $R^4$ not being H conforming to the general formula (E):

[—X—Y—S—]     (E)

wherein X is any one of

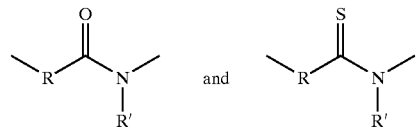

R is $(C.R^{20}.R^{21})_m$, wherein m is 0, 1, 2 or 3 and $R^{20}$ and $R^{21}$ are H, halogen or $C_1$–$C_{10}$ aliphatic hydrocarbyl group and is the same or different on each carbon;
Y is $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;
R' is H, $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;
wherein S is conjugated to the second calixarene moiety G.

5. The dimer of claim 4 wherein the second calixarene moiety G is of the general formula "(I)" or (III).

6. The dimer of claim 5 wherein the S group of the first calixarene moiety is conjugated to the S group of the second calixarene moiety through a spacer group, the spacer group being $C_1$–$C_6$ aliphatic hydrocarbyl group, $C_6$–$C_{10}$ aryl group, $C_6$–$C_{16}$ hydrocarbylaryl group any of which may be optionally substituted by one of more halo or oxo groups or interrupted by one or more oxo or amide groups.

7. The dimer of claim 1 wherein the S group of the first calixarene is conjugated directly to the S group of the second calixarene.

8. The dimer of claim 1 wherein X is (CH$_2$)CONH and Y is an aliphatic hydrocarbyl group.

9. The dimer of claim 8 wherein Y is an ethyl group.

10. The dimer of claim 1 wherein L is [—CH$_2$—] between each of the aryl groups.

11. The dimer of claim 1 wherein $R^5$ is a tertiary butyl group.

12. The dimer of claim 1 wherein the carboxy group $R^1$ conforms to the general formula (B):

[-Z-COOR$^{10}$]  (B)

wherein Z is a $C_1$, a $C_2$ or a $C_3$ carbon chain which is apart of an aliphatic hydrocarbyl group, aryl group or hydrocarbylaryl group, any of which is optionally substituted by one or more halo, oxo or nitro groups; and $R^{10}$ is H or a protecting group being a salt or an ester group.

13. The dimer of claim 12 wherein $R^{10}$ is H and the aliphatic hydrocarbyl group, aryl group or hydrocarbylaryl group of formula (B) are substituted by one or more groups which cause a reduction in the pKa of the carboxylic acid group with respect to an unsubstituted molecule.

14. The dimer of claim 1 wherein $R^1$ is of the general formula (C):

[—(C.R$^6$.R$^7$)$_n$—COOR$^{10}$]  (C)

wherein n is 1, 2 or 3 and $R^6$ and $R^7$ are H or halogen and is the same or different on each carbon and $R^{10}$ is H or a protecting group being a salt or an ester group.

15. The dimer of claim 1 wherein $R^1$ is of the general formula (D):

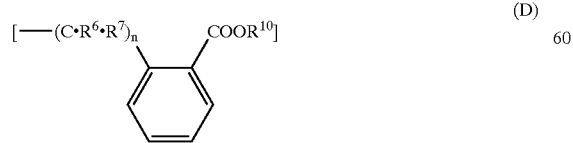

(D)

wherein n is 0 or 1 and $R^6$ and $R^7$ are H or halogen and is the same or different on each carbon and wherein the phenyl ring of the benzoic acid group is optionally substituted by one or more halo, oxo or nitro groups; and $R^{10}$ is H or a protecting group being a salt or an ester group.

16. The dimer of claim 15 wherein $R^{10}$ is H and the phenyl ring of the benzoic acid of formula (D) is substituted by one or more groups which cause a reduction in the pKa of the carboxy group with respect to an unsubstituted molecule.

17. The dimer of claim 14 wherein n is 1 and $R^6$ and $R^7$ are both H.

18. The dimer of claim 1 comprising formula (V)

formula (V)

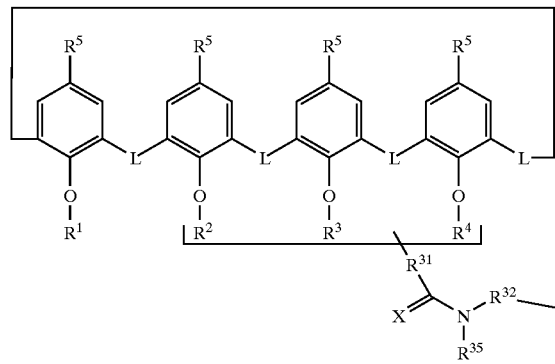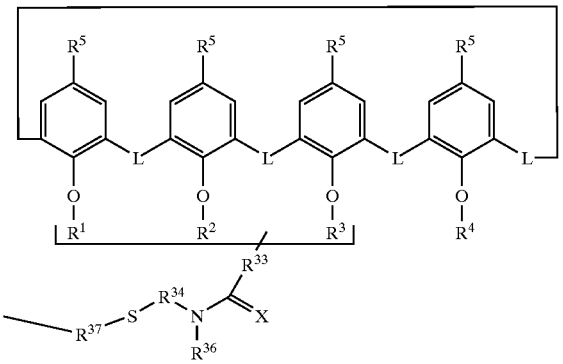

wherein

L is (—CH$_2$—) or [—O—CH$_2$—O—] and is the same or different between each aryl group;

$R^5$ is H, NO$_2$, halogen, or $C_1$–$C_{10}$ aliphatic hydrocarbyl group, $C_6$–$C_{20}$ aryl group, $C_6$–$C_{20}$ aryl group, $C_6$–$C_{20}$ hydrocarbylaryl group, any of which is optionally substituted by one or more halo or oxo groups or interrupted by one or more oxo or amide groups, and $R_5$ is the same or different on each aryl group;

$R^1$ is the same or different on each calixarene moiety comprises a carboxy group which is or is not protonated or protected;

two groups out of $R^2$, $R^3$ and $R^4$ on each calixarene moiety are H;

the one group out of $R^2$, $R^3$ and $R^4$ not being H on each calixarene moiety is the respective one of $R^{31}$ and $R^{33}$;

$R^{31}$ and $R^{33}$ are the same or different and are $C_1$–$C_{10}$ aliphatic hydrocarbyl group, $C_6$–$C_{10}$ aryl group or $C_6$–$C_{20}$ hydrocarbylaryl group, any of which is optionally substituted by one or more halo or oxo groups or interrupted by one or more oxo or amide groups; or (C.R$^{20}$.R$^{21}$)$_m$, wherein m is 0, 1, 2 or 3 and $R^{20}$ and $R^{21}$ are H, halogen or $C_1$–$C_{10}$ aliphatic hydrocarbyl group and is the same or different on each carbon;

$R^{35}$ and $R^{36}$ are the same or different and are $C_1$–$C_{10}$ aliphatic hydrocarbyl group, $C_6$–$C_{10}$ aryl group or $C_6$–$C_{20}$ hydrocarbylaryl group, any of which is optionally substituted by one or more halo or oxo groups or interrupted by one or more oxo or amide groups;

$R^{32}$ and $R^{34}$ are the same or different and are $C_1$–$C_{10}$ aliphatic hydrocarbyl group, $C_6$–$C_{10}$ aryl group or $C_6$–$C_{20}$ hydrocarbylaryl group, any of which is optionally substituted by one or more halo or oxo groups or interrupted by one or more oxo or amide groups;

X' on each calixarene moiety are the same or different, and are O or S moieties; and $R^{37}$ is an optional spacer group, which when present is $C_1$–$C_6$ aliphatic hydrocarbyl group, $C_6$–$C_{10}$ aryl group or $C_6$–$C_{16}$ hydrocarbylaryl group any of which may be optionally substituted by one or more halo or oxo groups or interrupted by one or more oxo or amide groups.

19. The dimer of claim 1 wherein some or all of the phenyl groups of the first or second calixarene moieties are further peripherally substituted.

20. A sensor comprising the calixarene dimer of claim 1.

21. The sensor of claim 20 further comprising a substrate, wherein the calixarene is adsorbed onto the surface of the substrate.

22. The sensor of claim 21 wherein the substrate comprises one or more metals.

23. The sensor of claim 22 wherein the substrate comprises gold.

24. A method of sequestering metals comprising contacting the metals with the calixarene dimer of claim 1.

25. The method of claim 24 wherein the method is carried out at a pH of between about 2 and about 11.

26. The method of claim 24 wherein the pH at which the method is carried out is buffered.

27. The method of claim 24 comprising:
(i) dissolving the calixarene in a hydrophobic organic solvent;
(ii) mixing the organic solvent with an aqueous phase containing metal ions;
(iii) agitating the organic solvent and aqueous phase together; and
(iv) recovering the metal from the organic phase.

28. The method of claim 24 wherein the metal is selected from the group consisting of U, Cd, Sr, Ca, a Lanthanide and Lu.

29. A process for preparing the calixarene dimer of claim 1 comprising conjugating two calixarene molecules using crystamine dihydrochloride.

30. A calixarene dimer of the general formula I-G comprising a first calixarene moiety of general formula I and a second calixarene moiety G, formula (I-G)

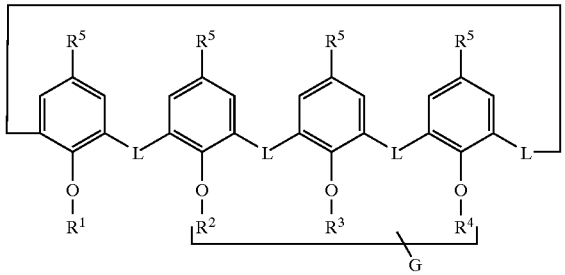

wherein:
L is [—$CH_2$—] or [—O—$CH_2$—O—] and is the same or different between each aryl group;
$R^5$ is H, $NO_2$, halogen, or $C_1$–$C_{10}$ aliphatic hydrocarbyl group, $C_6$–$C_{20}$ aryl group, $C_6$–$C_{20}$ aryl group, $C_6$–$C_{20}$ hydrocarbylaryl group, any of which is optionally substituted by one or more halo or oxo groups or interrupted by one or more oxo or amide groups, and $R_5$ is the same or different on each aryl group;

$R^1$ comprises a carboxy group which is not protonated or protected;

two groups out of $R^2$, $R^3$ and $R^4$ are H;

the one group out of $R^2$, $R^3$ and $R^4$ not being H comprises at least one atom of one or both of O and S, the atom being capable of causing the calixarene to be absorbed onto the surface of the substrate; and the one group out of $R^2$, $R^3$ and $R^4$ not being H is conjugated to the second calixarene moiety, G, wherein the structure of the first calixarene moiety is known as formula (III), the one group of $R^2$, $R^3$ and $R^4$ not being H conforming to the general formula (E):

[—X—Y—S—]    (E)

wherein X is any one of

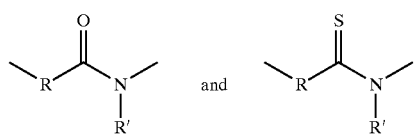

R is $(C.R^{20}.R^{21})_m$, wherein m is 0, 1, 2 or 3 and $R^{20}$ and $R^{21}$ are H, halogen or $C_1$–$C_{10}$ aliphatic hydrocarbyl group and is the same or different on each carbon, Y is $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

R' is H, $C_1$–$C_{10}$ aliphatic hydrocarbyl group, $C_6$–$C_{10}$ aryl group or $C_6$–$C_{20}$ hydrocarbylaryl group, any of which may be optionally substituted by one or more halo or oxo groups or interrupted by one or more oxo or amide groups;

wherein S is conjugated to the second calixarene moiety G.

31. The dimer of claim 30 wherein the second calixarene moiety G is of the general formula (I) or (III).

32. The dimer of claim 31 wherein the S group of the first calixarene moiety is conjugated to the S group of the second calixarene moiety through a spacer group, the spacer group being $C_1$–$C_6$ aliphatic hydrocarbyl group, $C_6$–$C_{10}$ aryl group, $C_6$–$C_{16}$ hydrocarbylaryl group any of which may be optionally substituted by one of more halo or oxo groups or interrupted by one or more oxo or amide groups.

33. A calixarene dimer of the general formula I-G comprising a first calixarene moiety of general formula I and a second calixarene moiety G, formula (I-G)

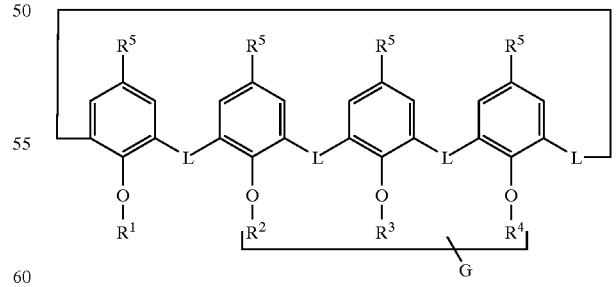

wherein:
L is [—$CH_2$—] or [—O—$CH_2$—O—] and is the same or different between each aryl group;
$R^5$ is H, $NO_2$, halogen, or $C_1$–$C_{10}$ aliphatic hydrocarbyl group, $C_6$–$C_{20}$ aryl group, $C_6$–$C_{20}$ aryl group, $C_6$–$C_{20}$ hydrocarbylaryl group, any of which is optionally substituted by one or more halo or oxo groups or interrupted by one or more oxo or amide groups, and $R_5$ is the same or different on each aryl group;

$R^1$ comprises a carboxy group which is not protonated or protected;

two groups out of $R^2$, $R^3$ and $R^4$ are H;

the one group out of $R^2$, $R^3$ and $R^4$ not being H comprises at least one atom of one or both of O and S, the said at least one atom being capable of causing the calixarene to be adsorbed onto the surface of the substrate; and the one group out of $R^2$, $R^3$ and $R^4$ not being H is conjugated to the second calixarene moiety, G, wherein the S group of the first calixarene is conjugated directly to the S group of the second calixarene.

34. A calixarene dimer of the general formula I-G comprising a first calixarene moiety of general formula I and a second calixarene moiety G,

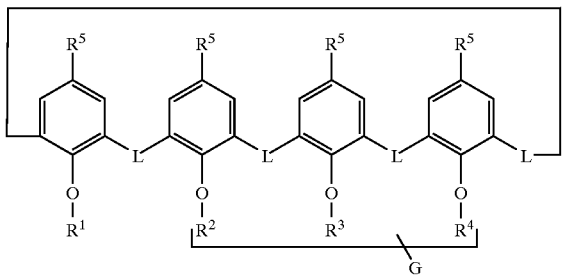

formula (I-G)

wherein:

L is [—$CH_2$—] or [—O—$CH_2$—O—] and is the same or different between each aryl group;

$R^5$ is H, $NO_2$, halogen, or $C_1$–$C_{10}$ aliphatic hydrocarbyl group, $C_6$–$C_{20}$ aryl group, $C_6$–$C_{20}$ aryl group, $C_6$–$C_{20}$ hydrocarbylaryl group, any of which is optionally substituted by one or more halo or oxo groups or interrupted by one or more oxo or amide groups, and $R_5$ is the same or different on each aryl group;

$R^1$ comprises a carboxy group which is not protonated or protected;

two groups out of $R^2$, $R^3$ and $R^4$ are H;

the one group out of $R^2$, $R^3$ and $R^4$ not being H comprises at least one atom of one or both of O and S, the said at least one atom being capable of causing the calixarene to be adsorbed onto the surface of the substrate; and the one group out of $R^2$, $R^3$ and $R^4$ not being H is conjugated to the second calixarene moiety, G, further comprising a substrate, wherein the calixarene is adsorbed onto the surface of the substrate and the substrate comprises gold.

* * * * *